(12) United States Patent
Guichard et al.

(10) Patent No.: US 7,777,030 B2
(45) Date of Patent: Aug. 17, 2010

(54) COMPOSITIONS AND METHODS FOR THE TREATMENT AND PREVENTION OF DISEASE

(75) Inventors: Gilles Guichard, Wolfishein (FR); Gersande Lena, Julienas (FR); Eliette Lallemand, Argenteuil (FR); Laurent Renia, Singapore (SG)

(73) Assignees: Centre National de la Recherge Scientifique (CNRS), Paris Cedex (FR); ImmuPharma France SA, Mulhouse Cedex (FR)

( * ) Notice: Subject to any disclaimer, the term of this patent is extended or adjusted under 35 U.S.C. 154(b) by 470 days.

(21) Appl. No.: 11/644,626

(22) Filed: Dec. 22, 2006

(65) Prior Publication Data

US 2007/0293469 A1    Dec. 20, 2007

Related U.S. Application Data

(60) Provisional application No. 60/755,631, filed on Dec. 29, 2005, provisional application No. 60/755,632, filed on Dec. 29, 2005, provisional application No. 60/755,626, filed on Dec. 29, 2005.

(51) Int. Cl.
*A61K 31/33* (2006.01)
(52) U.S. Cl. .......................... 540/484; 530/317; 540/1
(58) Field of Classification Search .................. 540/1, 540/484; 530/317
See application file for complete search history.

(56) References Cited

U.S. PATENT DOCUMENTS

| | | | |
|---|---|---|---|
| 3,637,811 | A | 1/1972 | Zenner |
| 4,003,912 | A | 1/1977 | Franz |
| 4,178,371 | A | 12/1979 | Morgan |
| 4,680,338 | A | 7/1987 | Sundoro |
| 4,918,186 | A | 4/1990 | Kajimoto |
| 4,929,736 | A | 5/1990 | Groutas |
| 5,508,400 | A | 4/1996 | Wilkerson |
| 5,532,356 | A | 7/1996 | Smyser |
| 5,532,357 | A | 7/1996 | Rodgers |
| 7,060,845 | B2 | 6/2006 | Guichard |
| 2005/0038105 | A1 | 2/2005 | Guichard |

FOREIGN PATENT DOCUMENTS

| | | |
|---|---|---|
| DE | 2847760 | 5/1980 |
| EP | 0533200 | 3/1993 |
| EP | 0765873 | 4/1997 |
| EP | 0858999 | 8/1998 |
| WO | WO 93/07128 | 4/1993 |
| WO | WO 93/09133 | 5/1993 |
| WO | WO 94/08977 | 4/1994 |
| WO | WO 94/22840 | 10/1994 |
| WO | WO 95/02582 | 1/1995 |
| WO | WO 96/29329 | 9/1996 |
| WO | WO 01/90083 | 11/2001 |
| WO | WO 01/96318 | 12/2001 |
| WO | WO 02/28842 | 4/2002 |
| WO | WO 03/103677 | 12/2003 |
| WO | WO 2007/074169 | 7/2007 |
| WO | WO 2007/074170 | 7/2007 |
| WO | WO 2007/074171 | 7/2007 |

OTHER PUBLICATIONS

English Abstract of JP 062,195,361, Feb. 1988.*
English Abstract of FR 002,810,039, Dec. 2001.*
Savarino A, Gennero L, Chen HC, Serrano D, Malavasi F, Boelaert JR, Sperber K. Anti-HIV effects of chloroquine: mechanisms of inhibition and spectrum of activity. AIDS Nov. 23, 2001;15(17):2221-9.
Savarino A, et al., The Anti-HIV-1 Activity of Chloroquine, Journal of Clinical Virology, vol. 20; Feb. 2001; pp. 131-135.
Morpurgo et al., N-hydroxysuccinimide Carbonates and Carbamates Are Useful Reactive Reagents for Coupleing Ligands to Lysines on Proteins. J. Biochem. Biophys. Methods, 38:17-28 (1999).
Kruijtzer et al., Approaches to the Synthesis of Ureapeptoid Peptidomimetics. Tetrahedron Letters, 38(30):5335-5338 (1997).
Richter et al., Curtius Degradation in Solid-Phase Synthesis. Tetrahedron Letters, 39:8747-8750 (1998).
Neel et al., Synthesis of a 3-Keto Bicyclic Pyrazolidinone Using a Curtius Rearrangement. Tetrahedron Letters, 37(28):4891-4894 (1996).
Conroy et al., Using the Electrostatic Field Effect to Design a New Class of Inhibitors for Cystein Proteases. Journal of the American Chemical Society, 119:4285-4291 (1997).
Shiori et al., Diphenylphosphoryl Azide. A New Convenient Reagent for a Modified Curtius Reaction and for the Peptide Synthesis. Journal of the American Chemical Society, 94:17 (1972).
Burgess et al., Solid Phase Synthesis of Oligoureas. Journal of the American Chemical Society, 119(7):1556-1564 (1997).
Corral et al., Synthesis of 5-amino-2,3-dihydro-1H-1,4-benzodiazepines. Journal of Heterocyclic Chemistry, 14:985 (1977).
Martinez et al., Activated N-Nitrosocarbamates for Regioselective Synthesis of N-Nitrosoureas. Journal of Medicinal Chemistry, 25:178-182 (1982).

(Continued)

*Primary Examiner*—David Lukton
(74) *Attorney, Agent, or Firm*—McCarter & English, LLP

(57) ABSTRACT

The present invention relates to various novel substituted dipeptide derived nitrogen-containing heterocyclic compounds, their pharmaceutically acceptable salt derivatives, and their methods of use. In one aspect the present invention relates to compositions and methods for the treatment and prevention of disease in a mammal comprising administering the compounds of the invention in a pharmaceutically acceptable form to a mammal. In particular, the invention relates to medicaments comprising various novel substituted dipeptide derived nitrogen-containing heterocyclic compounds and pharmaceutically acceptable salt derivatives and methods for administration to a mammal for the treatment and prevention of malarial diseases. The compounds of the invention may optionally be administered with at least one pharmaceutically acceptable excipient, another biologically active agent or a combination thereof.

7 Claims, 5 Drawing Sheets

OTHER PUBLICATIONS

Kim et al., The Solid Phase Synthesis of Oligoureas. Tetrahedron Letters, 37(30):5305-5308 (1996).

Wilson et al., An Efficient Synthesis of N,N-Linked Oligoureas. Tetrahedron Letter, 39(37):6613-6616 (1998).

Lena et al., "1,3,5-Triazepan-2,6-Diones As Structurally Diverse and Conformationaly Constrained Dipeptide Mimetics: Identification of Malaria Liver Stage Inhibitors From a Small Pilot Library," Chemistry—A European Journal, vol. 12 No. 33 Nov. 2006, pp. 8498-8512.

Semetey, Vincent et al. "O-Succinimidyl Carbamate Derivatives From Amino Acids and Peptides: A General Entry to Urea-Based Peptidomimetics," Proceedings of the European Peptide Symposium, 26th Montpellier, France, Sep. 10-15, 2003, Publisher: Editions EDK, Paris, Fr. Coden: 69EDWK; IS, 2003.

Boilard Eric et al. "Secreted Phospholipase A2 Inhibitors Are Also Potent Blockers of Binding to the M-Type Recepter," Biochemistry, 45(44), 13203-13218 Coden: Bichaw; ISSN: 0006-2960, 2006, XP002451620, p. 13212, compound 19.

Lin et al., Acyclic Structural Variants of Growth Hormone Secretagogue L-692,429; Bioorganic & Medicinal Chemistry Letters. 9(22):3237-3242 (1999).

Guichard et al., Effective Preparation of O-succinimidyl-2-(tert-butoxycarbonylamino)ethylcarbamate Derivatives from β-Aminio Acids. Application to the Synthesis of Urea-Containing Pseudopeptides and Oligoureas; Journal of Organic Chemistry. 64(23):8702-8705 (1999).

Guichard et al., Solid Phase Synthesis of Oligoureas Using 0-Succinimidyl-9H-Fluoren-9-ylmethoxycarbonylaminio)ethylcarbamate Derivatives As Activated Monomers. Tetrahedron Letters, 41(10):1553-1557 (2000).

Guha and Ramaswami, Attempts to Synthesize Uric Acid From Nine-Membered Cycloids. J. Indian Chem. Soc. 11:811-822 (1934).

Tamilarasu et al., Targeting RNA With Peptidomimetic Oligomers in Human Cells. Bioorganic and Medicinal Chemisitry Lettrs, 11(4):505-507.

Pankuch et al., N-Me-pAB-Glu-gamma-Glu-gamma-Tyr(3-NO2), An Internally Quenched Fluorogenic Gamma-Glutamyl Hydrolase Substrate. Bioorganic and Medicinal Chemistry Letters, 11(12):1561-1564 (2001).

Hintermann et al., Gamma-Peptides Forming More Stable Secondary Structures Than Alpha-Peptides: Synthesis and Helical NMR-Solution Structure of the Hexapeptide Analog of H-Val-Ala-Leu-$_2$OH. Helvetica Chimica Acta., 81:983-1002 (1998).

Boeijen et al., Solid Phase Synthesis of Oligourea Peptidomimetics. Euro. J. Organic Chem. 9:2127-21135 (1999).

Hemmerlin et al., Helix-Forming Oligoureas: Temperature-Dependent NMR, Structure Determination, and Circular Dichroism of a Nonamer With Functionalized Side Chains. 85(11):3692-3711 (2002).

Patch and Barron, Mimicry of Bioactive Peptides Via Non-Natural, Sequence-specific Peptidomimetic Oligomers, Current Opinion in Chemical Biology, 6:872-877 (2002).

Hamuro et al., De Novo Design of Antibacteral β-Peptides, J. Am. Chem. Soc., 121:12200-12201 (1999).

Liu et al., De Novo Design, Synthesis, and Characterization of Antimicrobial β-Peptides, J. Am. Chem. Soc., 123:7553-7559 (2001).

Arvidsson et al., On the Antimicrobial and Hemolytic Activities of Amphiphilic β-Peptides; Chem. Biochem., 2:771-773 (2001).

Porter et al., Non-Haemolytic β-amino-acid Oligomers, Nature, 404:565 (2000).

Porter et al., Mimicry of Host-Defense Peptides by Unnatural Oligomers: Antimicrobial β-Peptides, J. Am. Chem. Soc., 124:7324-7330 (2002).

Boeijen, et al., Solid-Phase Synthesis of Oligourea Peptidomimetics Employing the Fmoc Protection Strategy, J. Org. Chem, vol. 66, pp. 8454-8462 (2001).

* cited by examiner

6  $R^5$ = Bn             50-66%
7  $R^5$ = $CH_2CO_2tBu$  73-82%

8  $R^5$ = Bn             50-94%
9  $R^5$ = $CH_2CO_2tBu$  64-92%

COMPOSITIONS AND METHODS FOR THE TREATMENT AND PREVENTION OF DISEASE

CROSS-REFERENCE TO RELATED APPLICATIONS

Under 35 U.S.C. §119(e) this application claims the benefit of U.S. Provisional Patent Ser. No. 60/755,631, filed Dec. 29, 2005, and titled "Compositions and Methods for Synthesizing Novel Heterocyclic Therapeutics"; U.S. Provisional Patent Ser. No. 60/755,632, filed Dec. 29, 2005, and titled: "Compositions and Methods for Treatment and Prevention of Disease"; and U.S. Provisional Patent Application Ser. No. 60/755,626, filed Dec. 29, 2005, and titled "Compositions and Methods for the Inhibition of Phospholipase A2"; all of which are incorporated herein by reference in their entirety.

The present invention is related to U.S. nonprovisional patent applications "Compositions and Methods for the Inhibition of Phospholipase A2" filed Dec. 22, 2006 (Express Mail No.: EV 902583388 US) and "Compositions and Methods for Synthesizing Heterocyclic Therapeutic Compounds" filed Dec. 22, 2006 (Express Mail No.: EV 902583374 US), both of which are incorporated herein by reference in their entirety.

FIELD OF THE INVENTION

The present invention relates to compositions and methods for the treatment and prevention of disease in a mammal. In particular, the invention relates to medicaments comprising various novel substituted dipeptide derived nitrogen-containing heterocyclic compounds and pharmaceutically acceptable salt derivatives. The compounds of the invention may optionally be administered with at least one pharmaceutically acceptable excipient, another biologically active agent or a combination thereof.

BACKGROUND

Approximately 40% of the world's population lives in areas where a significant risk of contracting malaria exists. Each year, 300-500 million people suffer from acute malaria, and 0.5-2.5 million die from the disease. Although malaria has been widely eradicated in many parts of the world, the global number of cases continues to rise. The most important reason for this alarming situation is the rapid spread of malaria parasites that are resistant to antimalarial drugs, especially chloroquine, which is by far the most frequently used.

The research and development of new antimalarial drugs has been largely neglected since the 1970s owing to the end of colonialism, changes in the areas of military engagement, and the restricted market potential. Currently, few drugs against the malaria liver stage parasites are available. Because of technical difficulties, low yield and the complexity of the setting necessary to produce liver stage parasites, no new drugs are assessed systematically against these stages. Nevertheless, liver stages are a strong potential for drug targeting because; a) they possess a more complex and distinct metabolism than their blood stage counterpart, and b) they precede the pathogenic blood stage and thus offer prophylactic possibilities against malaria. Thus, the evaluation of new drugs against the liver stage offers new therapeutic horizons.

An additional observation is that some antimalarial compounds, for example, chloroquine also exhibit anti-HIV-1 activity. (See, for example, Savarino A, Gennero L, Chen H C, Serrano D, Malavasi F, Boelaert J R, Sperber K. Anti-HIV effects of chloroquine: mechanisms of inhibition and spectrum of activity. AIDS 2001 Nov. 23; 15(17):2221-9; Savarino A, Gennero L, Sperber K, Boelaert J R. The anti-HIV-1 activity of chloroquine. J Clin Virol 2001 February; 20(3):131-5.

Thus, the need in society exists for new therapeutics, which demonstrate advantageous clinical efficacy for the treatment and/or prevention of malaria, as well as for drugs that may be useful for the treatment and/or prevention of HIV infection and/or AIDS.

SUMMARY OF THE INVENTION

The present invention relates to compounds and methods for synthesizing compounds, and pharmaceutically acceptable salts thereof, which are efficacious for the treatment and/or prevention of disease in an individual. In one aspect, the invention relates to dipeptide derived heterocyclic compounds synthesized using the methods of the invention.

In additional aspects, the invention relates to pharmaceutical compositions comprising effective amounts of said compounds, and to therapeutic methods comprising their administration to an individual in need thereof for the treatment and/or prevention of a disease.

Additional objects and advantages of the present invention will be apparent from the drawings, detailed description, examples of the preferred embodiments that follow, and are expressly included within the scope of the present invention.

DETAILED DESCRIPTION OF THE INVENTION

Figure 1:
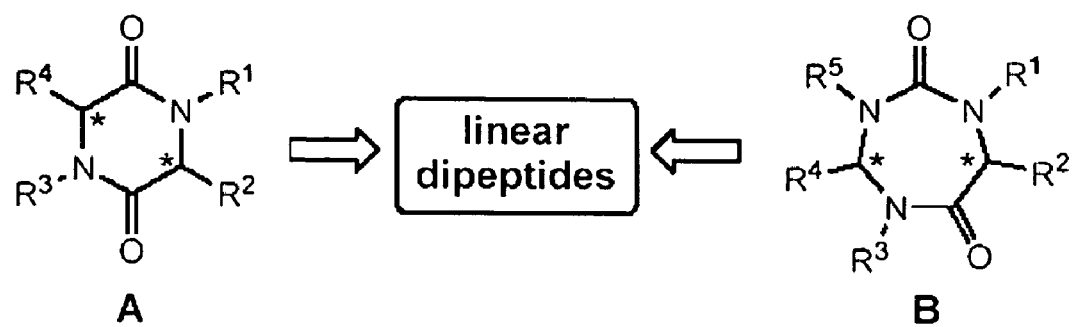
FIG. 1. Comparison of the 1,3,5-triazepan-2,6-dione scaffold, B, and 2,5-diketopiperazines, A.

When describing the compounds, compositions and methods of the invention, the following terms have the following meanings, unless otherwise indicated.

"Pharmaceutically acceptable salt" means those salts which retain the biological effectiveness and properties of the parent compounds and which are not biologically or otherwise harmful as the dosage administered. The compounds of this invention are capable of forming both acid and base salts by virtue of the presence of amino and carboxy groups respectively. Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl)carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "treatment" as used herein includes any treatment of a condition or disease in an animal, particularly a mammal, more particularly a human, and includes:

(i) preventing the disease or condition from occurring in a subject which has not yet been diagnosed as having it;

(ii) inhibiting the disease or condition, i.e. arresting its development; relieving the disease or condition, i.e. causing regression of the condition; or relieving the conditions caused by the disease, i.e. symptoms of the disease.

The term "therapeutically effective amount" refers to that amount which is sufficient to effect treatment, as defined herein, when administered to a mammal in need of such treatment. The therapeutically effective amount will vary depending on the subject and disease state being treated, the severity of the affliction and the manner of administration, and may be determined routinely by one of ordinary skill in the art.

"Heterocycle" refers to a heterocyclic group having from 4 to 9 carbon atoms and at least one heteroatom selected from the group consisting of N, O or S.

"Alkyl" refers to a branched or unbranched alkyl group having 1-6 carbon atoms, a branched or unbranched alkenyl group having 1-6 carbon atoms, a branched or unbranched alkinyl group having 1-6 carbon atoms.

"Hydroxyl" refers the functional group —OH when it is a substituent in an organic compound.

"Heterocyclic groups" can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO2-alkyl, —SO2-substituted alkyl, —SO2-aryl, oxo (=O), and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "thiol" refers to the group —SH.

The term "thioalkoxy" refers to the group —S-alkyl.

"Amino acid" refers to any molecule that contains both amino and carboxylic acid functional groups, and includes any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

"Amidine" refers to a functional group that has two amine groups attached to the same carbon atom with one carbon-nitrogen double bond: HN=CR'—NH"2.

"Alkoxyl" refers to an alkyl group linked to oxygen thus: R—O—, where R is an alkyl.

"Substituted alkyl" refers to a branched or unbranched alkyl, alkenyl or alkinyl group having 1-10 carbon atoms and having substituted by one or more substituents selected from the group consisting of hydroxyl, mercapto, carbylmercapto, halogen, carbyloxy, amino, amido, carboxyl, cycloalkyl, sulfo or acyl. These substituent generic groups having the meanings being identical with the definitions of the corresponding groups as defined herein.

"Halogen" refers to fluorine, bromine, chlorine, and iodine atoms.

"Acyl" denotes the group —C(O)R$_e$, where R$_e$ is hydrogen, alkyl, substituted alkyl, aryl, substituted aryl, arylalkyl, substituted arylalkyl, cycloalkyl, substituted cycloalkyl whereas these generic groups have meanings which are identical with definitions of the corresponding groups as defined in this legend.

"Acloxy" denotes the group —OAc, where Ac is an acyl, substituted acyl, heteroacyl or substituted heteroacyl whereas these generic groups have meanings which are identical with definitions of the corresponding groups as defined in this legend.

"Alkylamino" denotes the group —NR$_f$R$_g$, where R$_f$ and R$_g$, that are independent of one another, represent hydrogen, alkyl, substituted alkyl, aryl, substituted aryl, heteroaryl or substituted heteroaryl, whereas these generic substituents have meanings which are identical with definitions of the corresponding groups defined herein.

"Aryl" refers to an aromatic carbocyclic group having from 1 to 18 carbon atoms and being composed of at least one aromatic or multiple condensed rings in which at least one of which being aromatic.

"Substituted aryl" refers to an aromatic carbocyclic group having from 1 to 18 carbon atoms and being composed of at least one aromatic ring or of multiple condensed rings at least one of which being aromatic. The ring(s) are optionally substituted with one or more substituents selected from the group consisting of halogen, alkyl, hydroxyl, carbylmercapto, alkylamino, carbyloxy, amino, amido, carboxyl, nitro, mercapto or sulfo, whereas these generic substituent group have meanings which are identical with definitions of the corresponding groups as defined in this legend.

"Heteroaryl" refers to a heterocyclic group having from 4 to 9 carbon atoms and at least one heteroatom selected from the group consisting of N, O or S with at least one ring of this group being aromatic.

"Substituted heteroaryl" refers to a heterocyclic group having from 4 to 9 carbon atoms and at least one heteroatom selected from the group consisting of N, O or S with at least one ring of this group being aromatic and this group being substituted with one or more substituents selected from the group consisting of halogen, alkyl, carbyloxy, carbylmercapto, alkylamino, amido, carboxyl, hydroxyl, nitro, mercapto or sulfo, whereas these generic substituent group have meanings which are identical with definitions of the corresponding groups as defined in this legend.

"Carboxyl" denotes the group —C(O)OR$_j$, where R is hydrogen, alkyl, substituted alkyl, aryl, substituted aryl, heteroaryl or substituted heteroaryl, whereas these generic substituents have meanings which are identical with definitions of the corresponding groups defined herein.

"Cycloalkyl" refers to a monocyclic or polycyclic alkyl group containing 3 to 15 carbon atoms.

"Substituted cycloalkyl" refers to a monocyclic or polycyclic alkyl group containing 3 to 15 carbon atoms and being substituted by one or more substituents selected from the group consisting of halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P.

"Substituted heterocycloalkyl" refers to a monocyclic or polycyclic alkyl group containing 3 to 15 carbon atoms which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The term "alkenyl" refers to a monoradical of a branched or unbranched unsaturated hydrocarbon group preferably having from 2 to 40 carbon atoms, more preferably 2 to 10 carbon atoms and even more preferably 2 to 6 carbon atoms. Preferred alkenyl groups include ethenyl (—CH=CH2), n-propenyl (—CH2CH=CH2), iso-propenyl (—C(CH3)=CH2), and the like.

"Imidazole" refers to a heterocyclic base of the general formula: $C_3H_4N_2$.

"Aralkyl group" refers to, for example, a C1-C6 alkyl group which is attached to 1 or 2 aromatic hydrocarbon rings having from 6 to 10 carbon atoms and which has a total of 7 to 14 carbon atoms, such as the benzyl, alpha-naphthylmethyl, indenylmethyl, diphenylmethyl, 2-phenethyl, 2-alpha-naphthylethyl, 3-phenylpropyl, 3-alpha-naphthylpropyl, phenylbutyl, 4-alpha-naphthylbutyl or 5-phenylpentyl groups.

"Guanidine" refers generally to the amidine of amidocarbonic acid and has the general formula of: $C(NH_2)_3$.

The terms "aralkyl" and "heteroarylalkyl" refer to groups that comprise both aryl or, respectively, heteroaryl as well as alkyl and/or heteroalkyl and/or carbocyclic and/or heterocyloalkyl ring systems according to the above definitions.

In certain aspects the invention relates to nitrogen-containing heterocyclic compounds represented by the general formula I as follows:

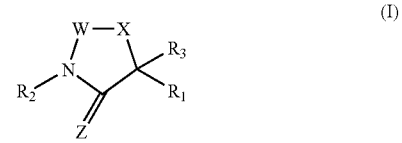

wherein, W is a member selected from the group consisting of —C(R$^5$)(R$^{5a}$)—; —C(R$^6$)(R$^{6a}$)—C(R$^7$)(R$^{7a}$)—; —C(R$^8$)=C(R$^9$)—; —N(R$^{10}$), and combinations thereof;

X is a member selected from the group consisting of —N(R$^{1a}$)C(=Y)N(R$^4$)—; —OC(=Y)N(R$^4$)—; —N(R$^{1a}$)C(=Y)O—; —N(R$^{1a}$)S(=O)N(R$^4$)—; —N(R$^{1a}$)S(=O)$_2$N(R$^4$)—; C(R$^{1a}$)(R$^{3a}$)C(=Y)N(R$^4$)—, and combinations thereof;

Y and Z represent, each independent from the other, a member selected from the group consisting of oxygen ("O") and sulfur ("S"); and R$^1$, R$^{1a}$, R$^2$, R$^3$, R$^{3a}$, R$^4$, R$^5$, R$^{5a}$, R$^6$, R$^{6a}$, R$^7$, R$^{7a}$, R$^8$, R$^9$, and R$^{10}$ represent, each independent from the other, a member selected from the group consisting of: a hydrogen atom; an amino acid side chain; a (C1-C10) alkyl; (C1-C10) alkenyl; (C1-C10) alkynyl; (C5-C12) monocyclic or bicyclic aryl; (C5-C14) monocyclic or bicyclic aralkyl; monocyclic or bicyclic (C5-C14) heteroaralkyl; and (C1-C10) monocyclic or bicyclic heteroaryl group having up to 5 heteroatoms selected from N, O, S, and P said groups being able to be non-substituted or substituted by 1 to 6 substituents further selected from the group consisting of: a halogen atom, an NO$_2$, OH, amidine, benzamidine, imidazole, 1,2,3-triazole, alkoxy, (C1-C4), amino, piperazine, piperidine, dialkylamino, guanidine group, bis alkylated or bis acylated guanido group, carboxylic acid, carboxamide, ester, hydroxamic acid, phosphinic acid, phosphonate, phosphonamidate, sulfhydryl and any combination thereof.

In any of the preferred embodiments, the compounds of the invention include the free base or acid forms, as well as salts thereof, of the dipeptide derivatived heterocyclics compounds described by the above formula. The invention also includes the optical isomers, analogs, and derivatives of the compounds described by the above formula. In a further embodiment of the invention, mixtures of enantiomers and/or diastereoisomers, resulting from a single preparative step, combination, or interconversion are encompassed. In yet a further embodiment of the invention, the compounds described by the formula I are included in a pharmaceutically acceptable form, and optionally include at least one other ingredient, for example a suitable carrier, excipient, another pharmaceutically active ingredient or a combination thereof.

The invention also provides prodrug forms of the above described analogs and derivatives, wherein the prodrug is metabolized in vivo to produce an analog or derivative as set forth above. Indeed, some of the above described analogs or derivatives may be a prodrug for another analog or derivative.

The term "prodrug" is well understood in the art and includes compounds that are converted to pharmaceutically active compounds in a biological system. For example, see *Remington's Pharmaceutical Sciences*, 1980, vol. 16, Mack Publishing Company, Easton, Pa., 61 and 424.

In another aspect of the invention, compositions containing the above described compounds are provided. Preferably, the compositions are formulated to be suitable for pharmaceutical or agricultural use by the inclusion of appropriate carriers or excipients.

In certain aspects, the intermediates and the desired compounds in the processes described can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

The present invention covers all possible isomers including tautomers and mixtures thereof. Where chiral carbons lend themselves to two different enantiomers, both enantiomers are contemplated as well as procedures for separating the two enantiomers.

In the case where a salt of a compound is desired and the compound is produced in the form of the desired salt, it can be subjected to purification as such. In the case where a compound is produced in the free state and its salt is desired, the compound is dissolved or suspended in a suitable organic solvent, followed by addition of an acid or a base to form a salt.

In other aspects, the present invention comprises pharmaceutically acceptable salts, racemates, and optical isomers thereof of formula I. The compounds of this invention typically contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

In a further aspect of the invention, methods for the use of the above described analogs and derivatives, as well as compositions, are provided. In certain embodiments, the method comprises administration to an individual of an effective amount of the compound of the invention for the treatment and/or prevention of a disease or condition, for example, cancer, osteoporosis, asthma, autoimmune diseases, HIV, AIDS, rheumatoid arthritis, systemic lupus erythematosus, Type I insulin-dependent diabetes, tissue transplantation, malaria, African sleeping sickness, Chagas disease, toxoplasmosis, psoriasis, restenosis, inhibition of unwanted hair growth as cosmetic suppression, hyperparathyroidism, inflammation, treatment of peptic ulcer, glaucoma, Alzheimer's disease, suppression of atrial tachycardias, stimulation or inhibition of intestinal motility, Crohn's disease and other inflammatory bowel diseases, high blood pressure (vasodilation), stroke, epilepsy, anxiety, neurodegenerative diseases, hyperalgesic states, protection against hearing loss (especially cancer chemotherapy induced hearing loss), and pharmacological manipulation of cocaine reinforcement and craving in treating cocaine addiction and overdose and other fungal bacterial, viral, and parasitic diseases.

The design and synthesis by combinatorial chemistry techniques of cyclic/polycyclic molecular frameworks that can efficiently distribute selected pharmacophores in the 3D space is an important method to identify small-molecules capable of modulating biological processes and for dissecting biological pathways. Molecules incorporating small or medium rings derived from peptides (e.g. 2, 5-diketopiperazines) are of particular interest owing to the facile access, the chemical and stereochemical diversity of peptide derivatives, as well as enhanced diversity resulting from appending operations.

Therapeutic Administration

In certain aspects, the present invention includes therapeutic compositions comprising the compounds of the invention in a pharmaceutically acceptable form. In still another of the preferred embodiments, the present invention includes methods for the treatment and/or prevention of disease in a mammal, for example, a human, comprising administering of an effective amount of a compound of the invention in a pharmaceutically acceptable form. The compound of the invention may optionally be administered together with at least one of a carrier, an excipient, another biologically active agent or any combination thereof.

Suitable routes for administration include oral, rectal, vassal, topical (including ocular, buccal and sublingual), vaginal and parental (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

In certain aspects, the invention relates to therapeutic compositions comprising from about 1% to about 100% by weight of the compounds of the invention. In any of the embodiments of the invention, the therapeutic compositions may be administered in a single daily dosage form or divided into two or more unitary dosage forms.

Unit dose forms are, for example, liquids, gels, coated tablets, tablets, ampoules, vials, suppositories or capsules. Other forms of administration are, for example, liquids, ointments, creams, pastes, foams, tinctures, drops, sprays, emulsions, suspensions, dispersions and the like. Examples are capsules containing from about 0.05 mg to about 1.0 g of the active ingredient. Unit dose forms can be administered by any pharmaceutically acceptable route widely known to those in the art including, for example, oral, enteral, parenteral, intravenous, nasal, anal, sublingual, by inhalation, vaginal, rectal, and the like.

The pharmaceutical compositions of the present invention are prepared in a manner known per se, for example by means of convential mixing, granulating, coating, dissolving or lyophilizing processes.

Preferably, solutions of the active ingredient, and in addition also suspensions or dispersions, especially isotonic aqueous solutions, dispersions or suspensions, are used, it being possible for these to be prepared before use, for example in the case of lyophilized compositions which comprise the active substance by itself or together with a carrier, for example mannitol. The pharmaceutical compositions can be sterilized and/or comprise excipients, for example preservatives, stabilizers, wetting agents and/or emulsifiers, solubilizing agents, salts for regulating the osmotic pressure and/or buffers, and they are prepared in a manner known per se, for example by means of convential dissolving or lyophilizing processes. The solutions or suspensions mentioned can comprise viscosity-increasing substances, such as sodium carboxymethylcellulose, carboxymethylcellulose, dextran, polyvinylpyrrolidone or gelatin.

Pharmaceutically acceptable forms include, for example, a gel, lotion, spray, powder, pill, tablet, controlled release tablet, sustained release tablet, rate controlling release tablet, enteric coating, emulsion, liquid, salts, pastes, jellies, aerosols, ointments, capsules, gel caps, or any other suitable form that will be obvious to one of ordinary skill in the art.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidinic acid, behenic acid or corresponding unsaturated acids, for example oleic acid, elaidic acid, euric acid, brasidic acid or linoleic acid, if appropriate with the addition of antioxidants, for example vitamin E, .beta.-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefosee, Paris), "Labrafil M 1944 CS" (unsaturated polyglycolated glycerides prepared by an alcoholysis of apricot kernel oil and made up of glycerides and polyethylene glycol esters; from Gattefosee, Paris), "Labrasol" (saturated polyglycolated glycerides prepared by an alcoholysis of TCM and made up of glycerides and polyethylene glycol esters; from Gattefosee, Paris) and/or "Miglyol 812" (triglyceride of saturated fatty acids of chain length $C_8$ to $C_{12}$ from Huls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol cellulose preparations and/or calcium phosphates, for example tricalcium phosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethylstarch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate.

By "controlled release" it is meant for purposes of the present invention that therapeutically active compound is released from the preparation at a controlled rate or at a specific site, for example, the intestine, or both such that therapeutically beneficial blood levels (but below toxic levels) are maintained over an extended period of time, e.g., providing a 12 hour or a 24 hour dosage form.

The term "rate controlling polymer" as used herein includes hydrophilic polymers, hydrophobic polymers or mixtures of hydrophilic and/or hydrophobic polymers that are capable of retarding the release of the compounds in vivo. In addition, many of the same polymers can be utilized to create an enteric coating of a drug, drug suspension, or drug matrix. It is within the skill of those in the art to modify the coating thickness, permeability, and dissolution characteristics to provide the desired controlled release profile (e.g., drug release rate and locus) without undue experimentation.

Examples of suitable controlled release polymers to be used in this invention include hydroxyalkylcellulose, such as hydroxypropylcellulose and hydroxypropylmethylcellulose; poly(ethylene)oxide; alkylcellulose such as ethycellulose and methylcellulose; carboxymethylcellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinylacetate phthalate; hydroxypropylmethylcellulose phthalate; hydroxypropylmethylcellulose acetate succinate; poly(alkyl methacrylate); and poly (vinyl acetate). Other suitable hydrophobic polymers include polymers or copolymers derived from acrylic or methacrylic acid esters, copolymers of acrylic and methacrylic acid esters, zein, waxes, shellac and hydrogenated vegetable oils.

To ensure correct release kinetics, the controlled release preparation of this invention contains about 5 and 75% by weight, preferably about 20 and 50% by weight, more preferably about 30 to 45% by weight controlled release polymer(s) and about 1 to 40% by weight, preferably about 3 to 25% by weight active compounds. The controlled release preparation according to the invention can preferably include auxiliary agents, such as diluents, lubricants and/or melting binders. Preferably, the excipients are selected to minimize the water content of the preparation. Preferably, the preparation includes an antioxidant. Suitable diluents include pharmaceutically acceptable inert fillers such as microcrystalline cellulose, lactose, dibasic calcium phosphate, saccharides, and/or mixtures of any of the foregoing. The diluent is suitably a water soluble diluent. Examples of diluents include microcrystalline cellulose such as Avicel ph112, Avicel pH101 and Avicel pH102; lactose such as lactose monohydrate, lactose anhydrous, and Pharmatose DCL 21; dibasic calcium phosphate such as Emcompress; mannitol; starch; sorbitol; sucrose; and glucose. Diluents are carefully selected to match the specific formulation with attention paid to the compression properties. Suitable lubricants, including agents that act on the flowability of the powder to be compressed are, for example, colloidal silicon dioxide such as Aerosil 200; talc; stearic acid, magnesium stearate, and calcium stearate. Suitable low temperature melting binders include polyethylene glycols such as PEG 6000; cetostearyl alcohol; cetyl alcohol; polyoxyethylene alkyl ethers; polyoxyethylene castor oil derivatives; polyoxyethylene sorbitan fatty acid esters; polyoxyethylene stearates; poloxamers; and waxes.

To improve the stability in the controlled release preparation, an antioxidant compound can be included. Suitable antioxidants include sodium metabisulfite; tocopherols such as alpha, beta, or delta-tocopherol tocopherol esters and alpha-tocopherol acetate; ascorbic acid or a pharmaceutically acceptable salt thereof; ascorbyl palmitate; alkyl gallates such as propyl gallate, Tenox PG, Tenox s-1; sulphites or a pharmaceutically acceptable salt thereof; BHA; BHT; and monothioglycerol.

The controlled release preparation according to the invention preferably can be manufactured by blending the compounds with the controlled release polymer(s) and auxiliary excipients followed by direct compression. Other methods for manufacturing the preparation include melt granulation. Preferred melt granulation techniques include melt granulation together with the rate controlling polymer(s) and diluent(s) followed by compression of the granules and melt granulation with subsequent blending with the rate controlling polymer(s) and diluents followed by compression of the blend. As desired prior to compression, the blend and/or granulate can be screened and/or mixed with auxiliary agents until an easily flowable homogeneous mixture is obtained.

Oral dosage forms of the controlled release preparation according to the invention can be in the form of tablets, coated tablets, enterically coated tablets or can be multiparticulate, such as in the form of pellets or mini-tablets. If desired, capsules such as hard or soft gelatin capsules, can contain the multiparticulates. If desired, the multiparticulate oral dosage forms can comprise a blend of at least two populations of pellets or mini-tablets having different controlled-release in vitro and/or in vivo release profiles. If desired, one of the pellet or mini-tablet populations can comprise immediate release multiparticulate, such as multiparticulates formed by conventional means.

If desired, the controlled release matrix tablets or multiparticulates of this invention can be coated with a controlled release polymer layer so as to provide additional controlled release properties. Suitable polymers that can be used to form this controlled release layer include the rate controlling polymers listed above.

As desired, the tablets, pellets or mini-tablets according to the invention can be provided with a light-protective and/or cosmetic film coating, for example, film-formers, pigments, anti-adhesive agents and plasticizers. Such a film former may consist of fast-dissolving constituents, such as low-viscosity hydroxypropylmethylcelluose, for example Methocel E5 or D14 or Pharmacoat 606 (Shin-Etsu). The film coating may also contain excipients customary in film-coating procedures, such as light-protective pigments, for example iron oxide, or titanium dioxide, anti-adhesive agents, for example talc, and also suitable plasticizers such as PEG 400, PEG 6000, and diethyl phthalate or triethyl citrate.

The controlled release polymer of this invention may consist of a hydrogel matrix. For instance, the compounds can be compressed into a dosage form containing a rate controlling polymer, such as HPMC, or mixture of polymers which when wet will swell to form a hydrogel. The rate of release from this dosage form is controlled both by diffusion from the swollen tablet mass and by erosion of the tablet surface over time. The rate of release may be controlled both by the amount of polymer per tablet and by the inherent viscosities of the polymers used.

Dyes or pigments can be admixed to the tablets or coated tablet coatings, for example for identification or characterization of different doses of active ingredient.

Pharmaceutical compositions, which can be used orally, are also hard capsules of gelatin and soft, closed capsules of gelatin and a plasticizer, such as glycerol or sorbitol. The hard capsules can contain the active ingredient in the form of granules, mixed for example with fillers, such as maize starch, binders and/or lubricants, such as talc or magnesium stearate, and stabilizers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilizers and detergents, for example of the polyethylene sorbitan fatty acid ester type.

Other oral forms of administration are, for example, syrups prepared in the customary manner, which comprise the active ingredient, for example, in suspended form and in a concentration of about 5% to 60%, preferably about 20% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parenteral administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilizers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example. Antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists, in particular, hydrocarbons, for example vaseline, paraffin oil or hard paraffin's, which preferably comprise suitable hydroxy compounds, such as fatty alcohol's or esters thereof, for example cetyl alcohol or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, the fatty alcohols. They also contain emulsifiers and/or additives mentioned in connection with the ointments which increase uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as corresponding nonionic emulsifiers, for example fatty acid esters of polyalcohols or ethyleneoxy adducts thereof, such as polyglyceric acid fatty acid esters or polyethylene sorbitan fatty esters (Tweens), and furthermore polyoxyethylene fatty alcohol ethers or polyoxyethylene fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments having secretion-absorbing powder constituents, such as metal oxides, for example titanium oxide or zinc oxide, and furthermore talc and/or aluminum silicates, which have the task of binding the moisture or secretions present.

Foams are administered from pressurized containers and they are liquid oil-in-water emulsions present in aerosol for. As the propellant gases, halogenated hydrocarbons, such as chlorofluoro-lower alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives, are admixed.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

It is understood that the examples and embodiments described herein are for illustrative purposes only and that various substitutions, modifications or changes in light thereof will be suggested to persons skilled in the art and are included within the spirit and purview of this application and are considered within the scope of the appended claims. The following examples are given by way of example of the preferred embodiments, and are in no way considered to be limiting to the invention. For example, the relative quantities of the ingredients may be varied to achieve different desired effects, additional ingredients may be added, and/or similar ingredients may be substituted for one or more of the ingredients described. All publications, patents, and patent applications cited herein are hereby incorporated by reference in their entirety for all purposes.

EXAMPLES

To expand further the skeletal diversity attainable with peptide substrates, a variety of compounds were synthesized and densely functionalized from, for example, a dipeptide-derived 1,3,5-triazepan-2,6-dione scaffold. These compounds were found to be active by screening a small "prospecting" library against the malaria liver stage (LS).

Interest in designing and evaluating the dipeptide-derived 1,3,5-triazepan-2,6-dione scaffold stems from the remarkable biological activities exhibited by molecules with diazepine and triazepine skeletons. In particular seven-membered cyclic ureas have attracted much attention in recent years with application in the development of HIV-protease and reverse transcriptase inhibitors, Factor Xa inhibitors, beta-lactamases inhibitors, phospholipase C inhibitors, and chemokine receptor antagonists.

Figure 2:
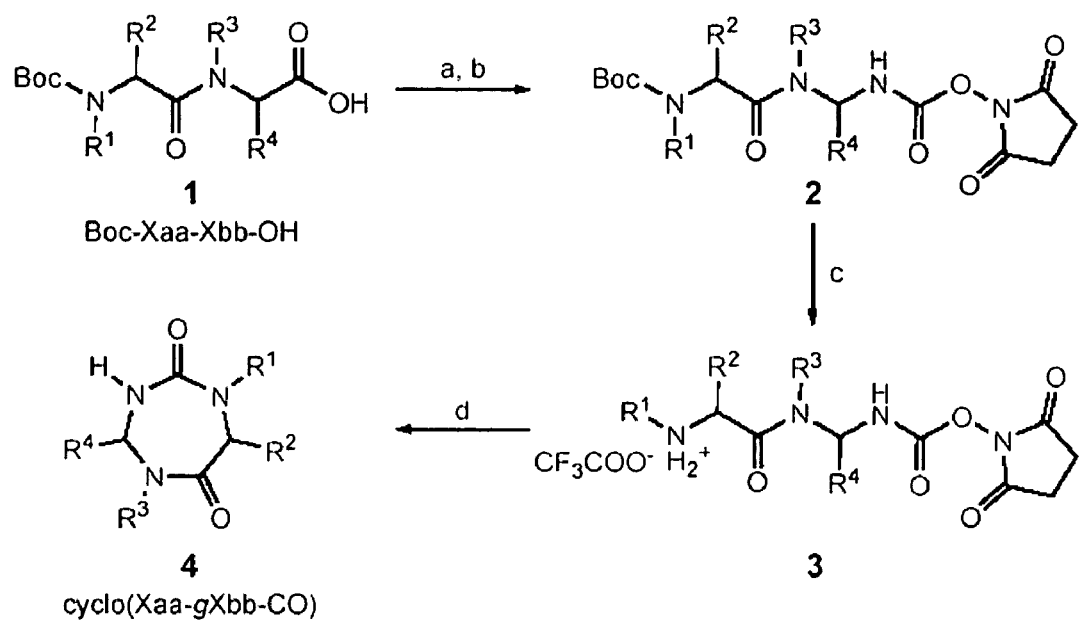
FIG. 2. a) EtOCOCl, NMM, THF, −20° C., then $NaN_3$ in $H_2O$; b) Toluene, 65° C., then HOSu and pyridine; c) TFA, 30 min; d) DIEA, MeCN; e) PS-DIEA, $CH_2Cl_2$. g=gem, refers to the 2-alkyl gem-diamino-derivative of the corresponding amino-acid according to the nomenclature proposed by Chorev and Goodman.

With reference to FIG. 2, 1,3,5-triazepan-2,6-diones 4 are constructed in only four steps by cyclization of simple activated dipeptide derivatives, and the approach benefits from the considerable diversity of commercial alpha-amino acids. The cyclization strategy parallels the previously reported approach to the preparation of enantiopure macrocyclic oligoureas. Succinimidyl carbamates 2 were prepared from Boc-dipeptides 1 as previously described for N-protected alpha- and beta-amino acids. Selective removal of the Boc group by treatment of crude 2 with trifluoroacetic acid (TFA) afforded 3 which cyclized to 4 in the presence of diisopropylethylamine (DIEA). The cyclization proceeded rapidly with concomitant release of N-hydroxysuccinimide and formation of the TFA salt of DIEA. These byproducts were removed by either recrystallization of crude 4, liquid-liquid extraction or polymer supported sequestration (PSS) with tris-(2-aminoethyl)amine polystyrene (PS-triamine). Alternatively polymer-supported-DIEA (PS-DIEA) was found to be very effective in promoting cyclization and simultaneously removing byproducts.

A set of 18 monocyclic to tetracyclic 1,3,5-triazepin-2,6-diones 4 was synthesized by this approach in moderate to high overall yield starting from a variety of dipeptide sequences (Table 1).

TABLE 1

Solution phase synthesis of 1,3,5-triazepan-2,6-diones (4) from dipeptides (1). (Bold numbers are in reference to FIG. 2).

| Entry | 1 | Xaa | Xbb | 3 Yield (%)[a] | 4 Yield (%)[b,c] |
|---|---|---|---|---|---|
| 1 | a | Phe | Sar | 93 | 71[d] |
| 2 | b | D-Phe | Sar | 78 | 74[d] |
| 3 | c | Val | Sar | 95 | 67[f] |
| 4 | d | Leu | Sar | 86 | 34[f] |
| 5 | e | Dap (Fmoc) | Sar | 72 | 43[f] |
| 6 | f | Phg | Sar | 58 | 41[f] |
| 7 | g | 2-Nal | Sar | 50 | 77[f] |
| 8 | h | Tic | Sar | 59 | 68[d] |
| 9 | i | Phe | Pro | 90 | 66[d] |
| 10 | j | D-Phe | Pro | 80 | 66[g] |
| 11 | k | 2-Nal | Pro | 82 | 78[d] |
| 12 | l | Tic | Pro | 77 | 57[d] |
| 13 | m | Phe | NMe-Phe | 34 | 97[d] |
| 14 | n | Phe | Hyp (Bn) | 73 | 99[f,h] |
| 15 | p | Ala | Tic | 54 | 97[i] |

TABLE 1-continued

Solution phase synthesis of 1,3,5-triazepan-2,6-diones (4) from dipeptides (1). (Bold numbers are in reference to FIG. 2).

| Entry | 1 | Xaa | Xbb | 3 Yield (%)[a] | 4 Yield (%)[b,c] |
|---|---|---|---|---|---|
| 16 | q | Pro | Val | 66 | 11[g,j] |
| 17 | r | Pro | Leu | 58 | 7[g,j] |

[a] overall yields from 1;
[b] yields from 3;
[c] cyclization performed using DIEA unless otherwise stated;
[d] purification by recrystallization;
[e] PS-DIEA used for cyclization;
[f] purification by flash chromatography (CH$_2$Cl$_2$/MeOH/AcOH, 97:3:1);
[g] purification by C$_{18}$ RP-HPLC;
[h] hydrogenation of the benzyl group afforded triazepan-dione 4 with a hydroxyl side chain in 70% yield;
[i] purification using PS-triamine;
[j] cyclization performed with N-methyl morpholine at a concentration of 0.001 M. The formation of 4 was accompanied by the formation of the corresponding cyclodimer.
Abbreviations:
Dap = diaminopropanoic;
Phg = Phenylglycine;
2-Nal = 2-naphthylphenylalanine;
Tic = Tetrahydroisoquinoline-3-carboxylic acid;
Hyp = cis-4-Hydroxyproline.

Carbamates 2a-n and 2p bearing a tertiary amide N-terminal to gXbb residue (R3≠H) were expected to give an equilibrium mixture between trans and cis isomers (a 1:1 ratio was observed for 2a by $^1$H-NMR in CD$_3$CN) and as a result readily cyclized to 4 (entries 1-15). In contrast, cyclization of precursors 2 with a secondary amide N-terminal to gXbb (R$^3$=H, entries 16 and 17) gave 4 together with various proportion of the corresponding 14-membered ring cyclodimer.

Figure 3:
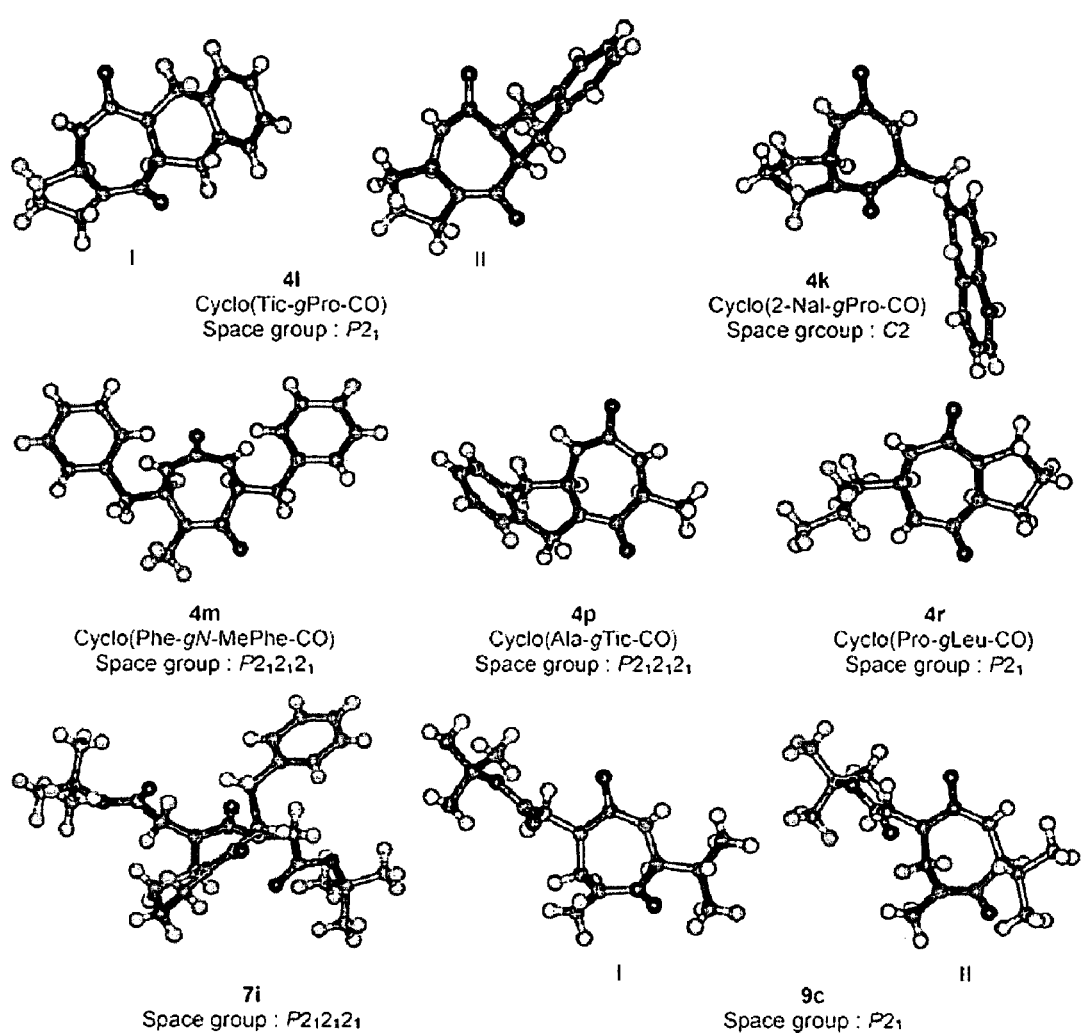
FIG. 3. X-ray crystal structures of representative 1,3,5-triazepan-2,6-diones 4, 7 and 9.

X-ray diffraction and $^1$H NMR studies of representative members of the library, revealed that the 1,3,5-triazepan-2,6-dione ring system in compounds 4 generally adopts a rigid non planar conformation (the values for the mean angle between the amide and urea planes is close to 120° with side chains R$^2$ and R$^4$ in pseudo-equatorial position (FIG. 3).

Figure 4:
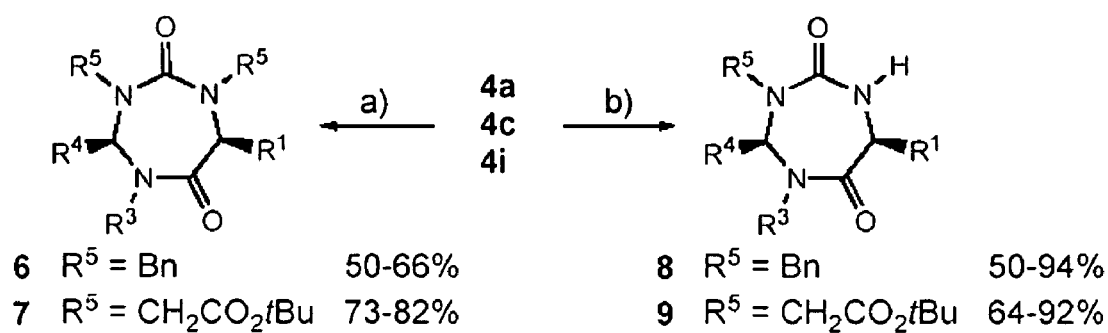
FIG. 4. a) NaH (4 equiv), RX (4 equiv); b) $KF/Al_2O_3$ (10 equiv) or NaH (2 equiv), RX (1.5 equiv).
Figure 5:
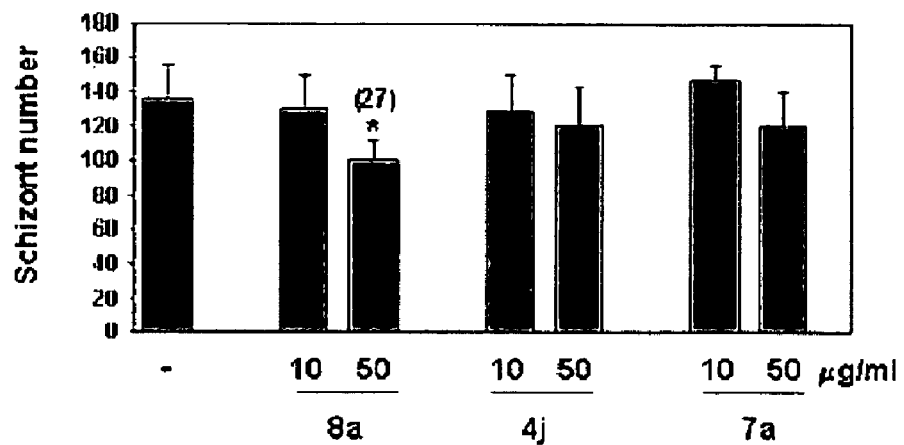
FIG. 5. Effect of selected 1,3,5-triazepan-2,6-diones on malaria liver stage development. Compounds were added at the time of sporozoite invasion and during liver stage development. Schizont number was estimated by counting this mature parasite forms in 48 hours cultures. Results are expressed as the mean ±SD of 3 triplicate cultures. Data are representative of 2 to 6 experiments per compounds tested. *, P<0.05, Mann-Whitney U test.
Figure 5:
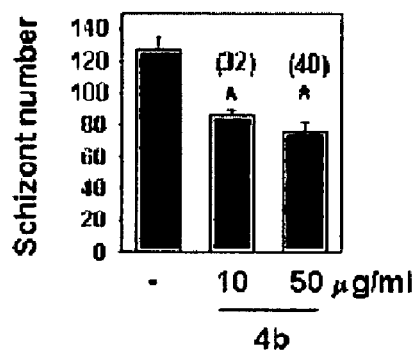
Figure 5:
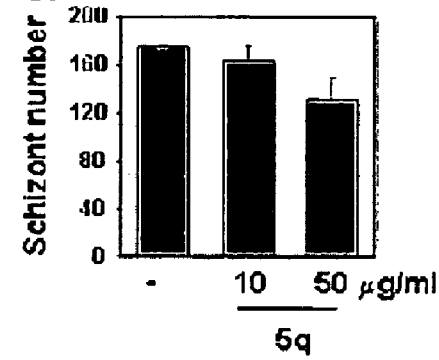

Further functionalization and diversification of parent scaffolds 4 was achieved by alkylation of urea nitrogens (FIG. 4). Treatment of scaffold 4 with NaH (5 equiv) and various electrophiles (3 equiv) afforded dialkylated cyclo-ureas (e.g. 6 and 7) in good yield and purities following liquid/liquid extraction and PSS of excess electrophile with N-(2-mercaptoethyl)aminomethyl-PS. Interestingly, in the presence of KF/Al$_2$O$_3$ or NaH (2 equiv.) cyclo(Xaa-gSar-CO) 4a, 4c and cyclo(Phe-gPro-CO) 4l were converted to 8 and 9 monoalkylated at the gem-diamino urea nitrogen with good to excellent selectivities (8:6 and 9:7 in the range 80:20 to 100:0). Crystal structures of dialkylated and monoalkylated derivatives 7 and 9(I), respectively, show a rearrangement of the ring geometry with R$^1$ side-chain now pointing in quasi axial orientation (FIG. 5).

Invasion of host hepatocytes by sporozoites represent an early step in the life cycle of the malaria parasite. Malaria liver stages hold great promise for drug targeting because i) they possess a more complex and distinct metabolism than their blood stage counterpart and ii) they precede the pathogenic blood stage, thus offering prophylaxis possibilities against malaria. However, very few drugs against LS parasites are available and most of them like primaquine display severe side-effects or loose efficiency due to the development of parasite resistance.

Seventeen different 1,3,5-triazepan-2,6-diones were randomly selected and were first tested at different doses for toxicity on primary mouse hepatocyte culture. From these, nine were shown to be toxic at all doses tested (6, 25-100 μg/ml) and two at high doses (over 50 μg/ml). The non toxic remaining six molecules were thus tested to evaluate their effects on sporozoite invasion and development in hepatocytes. Four of these 4j, 7a, 5q and 11 had no significant effect on liver parasites (FIG. 5A, 5C and data not shown). In contrast, two molecules, 4b and 8a, were shown to inhibit significantly and repeatedly LS development (FIGS. 5A and 5B), 4b being the most potent.

We have presented the design and the construction of a 32 members small library of dipeptide derived 1,3,5-triazepin-2,6-diones which led to the identification of two molecules active against the malaria liver stages exempt of toxicity on mouse hepatocytes. Studies aimed at increasing the structural diversity of the library by integrating a more comprehensive set of peptide precursors (including side-chain and stereochemical diversity) and appending processes are undergoing and should help for the rapid identification of more potent molecules to the underexplored stage of malaria.

Examples of General Synthetic Schemes and Procedures

Example 1

Synthesis of [1,3,5]Oxadiazepane-2,6-diones (Formula Ia)

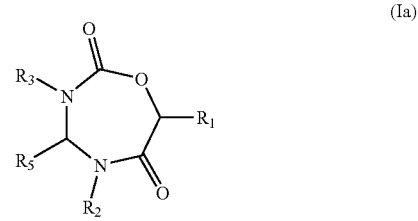

(Ia)

General Scheme Synthetic Scheme for Ia.

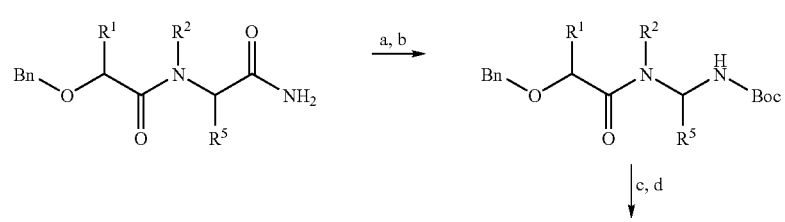

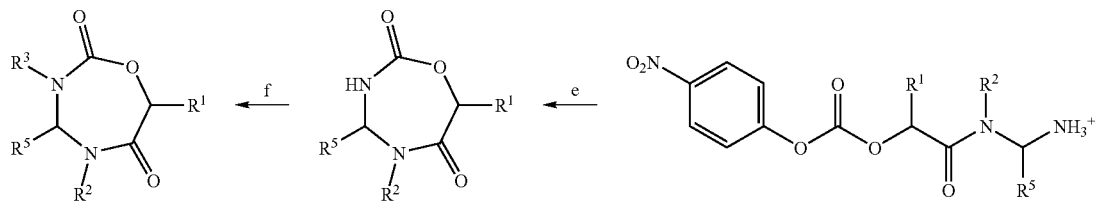

a) lobenzene bistrifluoroacetate (IBTFA), THF/H$_2$O; b) Boc$_2$O; c) p-nitrophenylchloroformate, CH$_2$Cl$_2$, Diisopropylethylamine; d) trifluoroacetic acid; e) DIEA, HOBt; f) NaH, R$^3$Br.

Example 2

Synthesis of 2-Thioxo-[1,3,5]triazepan-6-ones (Formula Ib)

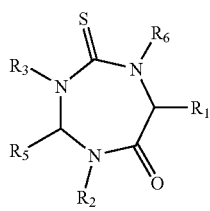
(Ib)

General Synthetic Scheme for Ib.

Step a) Dipeptide amide Ib-p1 was dissolved in THF/water (3:1) and treated with iodobenzene bistrifluoroacetate (IBTFA), THF/H$_2$O (1.2 equiv.) for 3 h, time after which starting material was consumed. Solvents were removed in vacuo and Et$_2$O was added. The solid which formed was collected and washed with Et$_2$O to yield the corresponding gem-diamino derivative which was used in the next step without further purification. Quantitative Yield.

Step b) bis(benzotriazol-1-yl)methanethione (1 equiv) was dissolved in CH2Cl2 at rt. The previously synthesized gem-diamino derivative was added dropwise and the reaction mixture was stirred for 18 h. Solvent was removed under vacuum and the residue was redissolved in EtOAc and washed with 5% aqueous sodium carbonate, water and brine before drying over anhydrous sodium sulphate. Solvent was removed under vacuum and 1b-p2 was recrystallized from ethyl acetate.

Step c) The 1-thiocarbamoylbenzotriazole was treated with TFA at 0° C. After 30 min, TFA was removed by co-evaporation with hexane and the TFA salt precipitated by addition of diethylether. The resulting salt Ib-p3 was collected by filtration and dried under high vacuum. It was used in the next step without further purification.

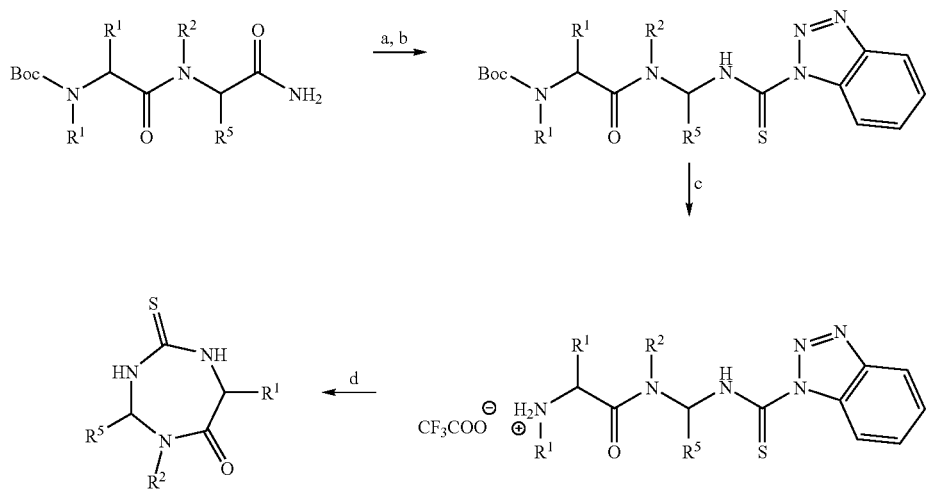

Step d) The TFA salt Ib-p3 was dissolved in MeCN and diisopropylethylamine (2.5 equiv) was then added and the reaction mixture was stirred for 24 h. Solvent was removed in vacuum and the residue was redissolved in EtOAc, washed with 5% aqueous sodium carbonate, 1M HCl, water, and brine before drying over anhydrous sodium sulphate. Solvent was removed in vacuum and cyclic Ib-1 was purified by recrystallization from $CH_2Cl_2$/diisopropyl ether.

Example 3

Synthesis of 4-Benzyl-6-methyl-[1,3,6]oxadiazocane-2,5-dione (Formula Ib-1)

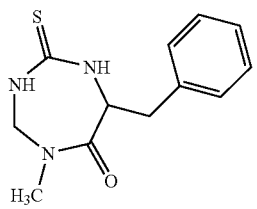
(Ib-1)

General Synthetic Scheme for Ib-1.

Step a) Dipeptide amide Ib-p1 was dissolved in THF/water (3:1) and treated with iodobenzene bistrifluoroacetate (IBTFA), $THF/H_2O$ (1.2 equiv.) for 3 h, time after which starting material was consumed. Solvents were removed in vacuo and $Et_2O$ was added. The solid which formed was collected and washed with $Et_2O$ to yield the corresponding gem-diamino derivative which was used in the next step without further purification. Quantitative Yield.

Step b) bis(benzotriazol-1-yl)methanethione (1 equiv) was dissolved in CH2Cl2 at rt. The previously synthesized gem-diamino derivative was added dropwise and the reaction mixture was stirred for 18 h. Solvent was removed under vacuum and the residue was redissolved in EtOAc and washed with 5% aqueous sodium carbonate, water and brine before drying over anhydrous sodium sulphate. Solvent was removed under vacuum and 1b-p2 was recrystallized from ethyl acetate.

Step c) The 1-thiocarbamoylbenzotriazole was treated with TFA at 0° C. After 30 min, TFA was removed by co-evaporation with hexane and the TFA salt precipitated by addition of diethylether. The resulting salt Ib-p3 was collected by filtration and dried under high vacuum. It was used in the next step without further purification.

Step d) The TFA salt Ib-p3 was dissolved in MeCN and diisopropylethylamine (2.5 equiv) was then added and the reaction mixture was stirred for 24 h. Solvent was removed in vacuum and the residue was redissolved in EtOAc, washed with 5% aqueous sodium carbonate, 1M HCl, water, and brine before drying over anhydrous sodium sulphate. Solvent

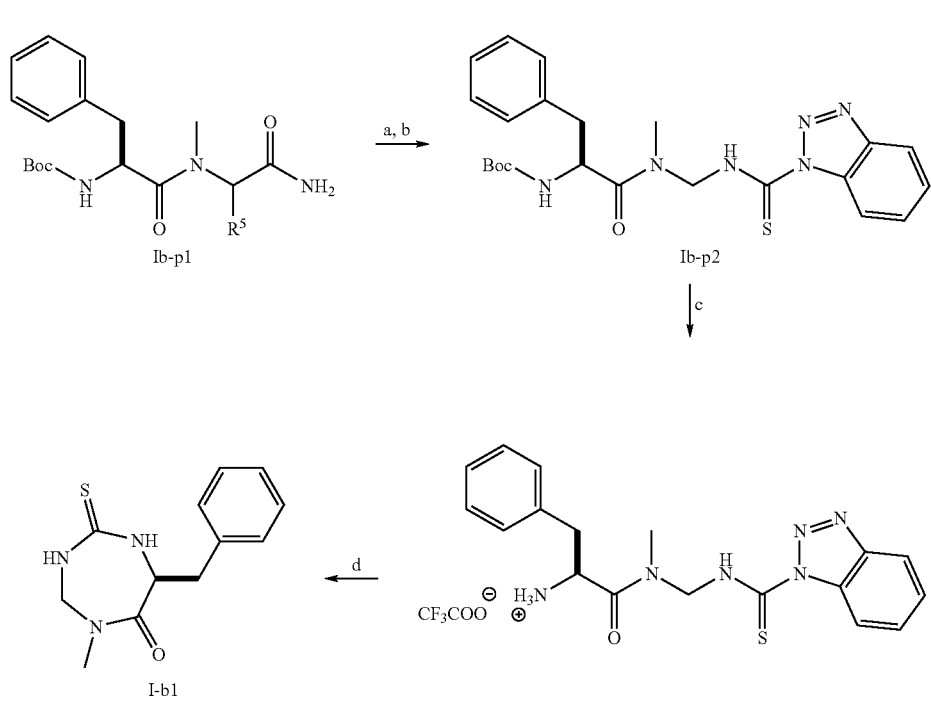

was removed in vacuum and cyclic Ib-1 was purified by recrystallization from CH₂Cl₂/diisopropyl ether.

Example 4

Synthesis of 2-Thioxo-[1,3,5]oxadiazepan-6-ones (Formula Ic)

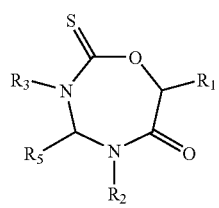
(Ic)

General Synthetic Scheme for Ic.

ture was stirred for 18 h. Solvent was removed under vacuum and the residue was redissolved in EtOAc and washed with 5% aqueous sodium carbonate, water and brine before drying over anhydrous sodium sulphate. Solvent was removed under vacuum and 1b-p2 was recrystallized from ethyl acetate.

Step c) The 1-thiocarbamoylbenzotriazole was treated with TFA at 0° C. After 30 min, TFA was removed by co-evaporation with hexane and the TFA salt precipitated by addition of diethylether. The resulting salt Ib-p3 was collected by filtration and dried under high vacuum. It was used in the next step without further purification.

Step d) The TFA salt Ib-p3 was dissolved in MeCN and diisopropylethylamine (2.5 equiv) was then added and the reaction mixture was stirred for 24 h. Solvent was removed in vacuum and the residue was redissolved in EtOAc, washed with 5% aqueous sodium carbonate, 1M HCl, water, and brine before drying over anhydrous sodium sulphate. Solvent was removed in vacuum and cyclic Ib-1 was purified by recrystallization from CH₂Cl₂/diisopropyl ether.

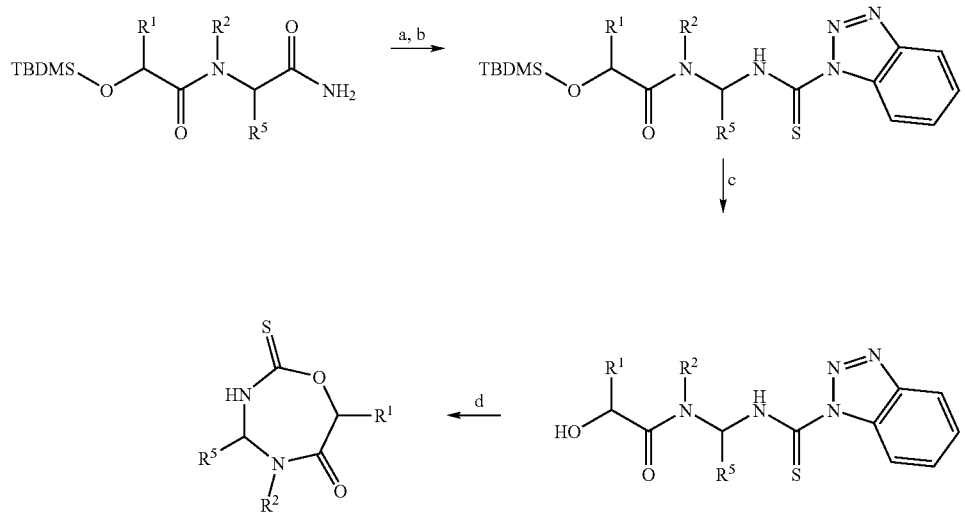

Step a) Dipeptide amide Ib-p1 was dissolved in THF/water (3:1) and treated with iodobenzene bistrifluoroacetate (IBTFA), THF/H₂O (1.2 equiv.) for 3 h, time after which starting material was consumed. Solvents were removed in vacuo and Et₂O was added. The solid which formed was collected and washed with Et₂O to yield the corresponding gem-diamino derivative which was used in the next step without further purification. Quantitative Yield.

Step b) bis(benzotriazol-1-yl)methanethione (1 equiv) was dissolved in CH2Cl2 at rt. The previously synthesized gem-diamino derivative was added dropwise and the reaction mix-

Example 5

Synthesis of [1,3,6]Oxadiaxocane-2,5-diones (Formula Id)

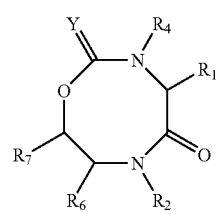
(Id)

23

General Synthetic Scheme for Id.

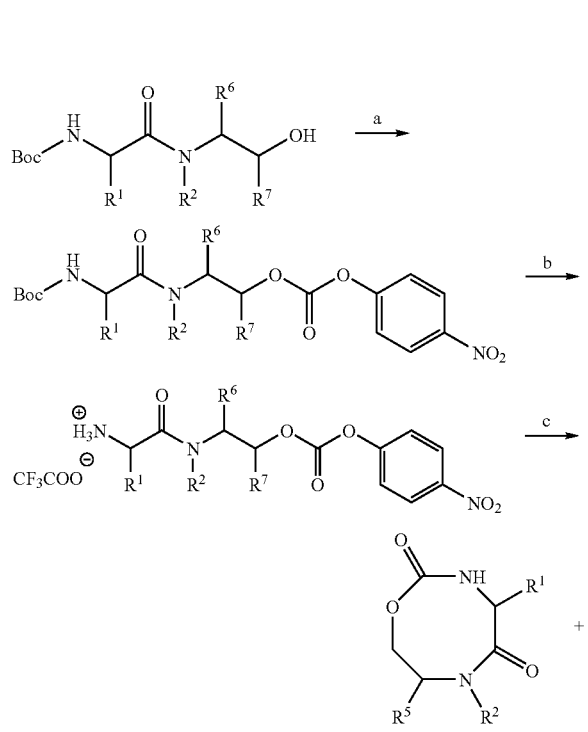

a) para-nitrophenyl chloroformate (2 eq), pyridine (1,1 eq), CH2Cl2, TA overnight; b) TFA, TA 30 minutes; c) DIEA (2,6 eq), HOBt, (1 eq), MeCN, TA 3 jours.

Example 6

Synthesis of 4-Benzyl-6-methyl-[1,3,6]oxadiazocane-2,5-dione (Formula Id-1)

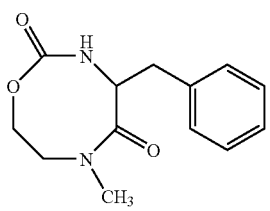
(Id-1)

General Synthetic Scheme for Id-1.

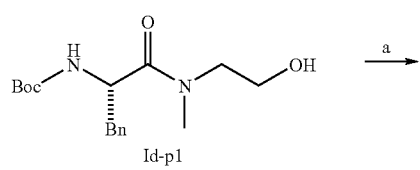

24

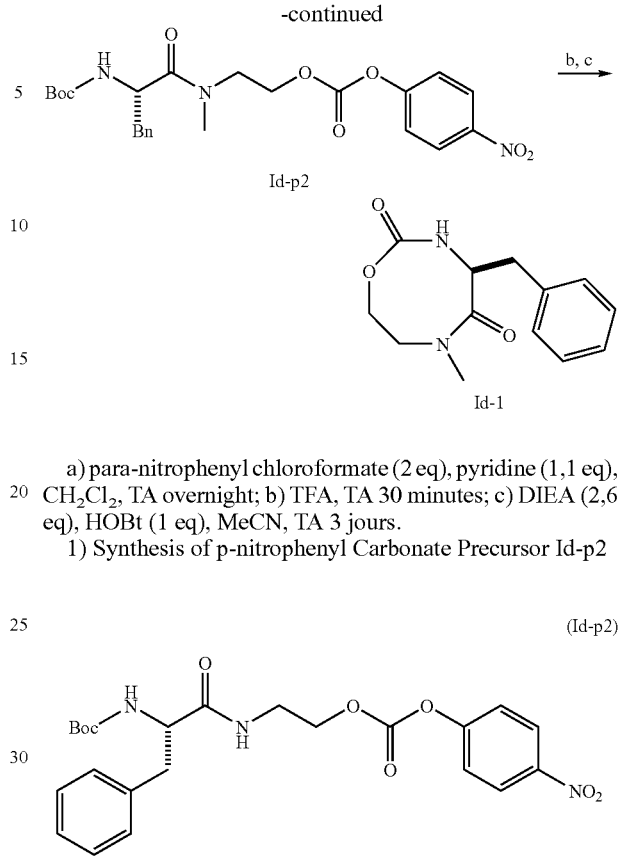

a) para-nitrophenyl chloroformate (2 eq), pyridine (1,1 eq), CH$_2$Cl$_2$, TA overnight; b) TFA, TA 30 minutes; c) DIEA (2,6 eq), HOBt (1 eq), MeCN, TA 3 jours.

1) Synthesis of p-nitrophenyl Carbonate Precursor Id-p2

(Id-p2)

The starting dipeptide alcohol Id-p1 (300 mg, 0.93 mmol, 1 eq) is dissolved in 5 mL CH$_2$Cl$_2$ and 82 μL pyridine (1.02 mmol, 1.1 eq). A solution of 4-nitrophenyl chloroformate (0.37 g, 1.86 mmol, 2 eq) in 2 mL.

After stirring for 24 h, the reaction mixture is diluted with 15 mL CH$_2$Cl$_2$, and washed with 1N NaHCO$_3$. The organic phase is dried on Na$_2$SO$_4$, concentrated and purified by flash chromatography (eluant 1:2 AE/cyclohexane) to yield pure carbonate Id-p2 with 59% yield. HPLC tR 14.1 (gradient 30-100% B, 20 min.)

$^1$H NMR (300 MHz, CDCl$_3$) δ 8.3 (m, 2H, arom-H α-NO2), 7.39 (m, 2H, arom-H β-NO2), 7.24 (m, 5H, arom-H), 5.34 (m, J=10.55 Hz, 1H NH), 4.85 (q, J=14.9, 7.9 Hz, 1H α-NH), 4.31 4.14 (dd, J=9.97, 5.1 Hz, 2H α-O), 3.77 3.54 (dd, J=14.5, 5.2 Hz, 2H α-NMe), 2.98 (m, 2H α-Phe), 2.79 (s, 3H NMe), 1.43 (s, 9H Boc).

$^{13}$C NMR (100 MHz, CDCl3) δ 171.8 (CO amide), 154.8 (CO carbamate), 154.5 (CO carbonate), 151.6 (C arom α-NO$_2$), 144.8 (C arom δ-NO2), 135.5 (C arom Phe), 128.8 (2CH Phe), 128.7 (2CH Phe), 127.8 (CH-Phe), 124.7 (CH arom), 121.1 (CH-arom), 79.3 (C Boc), 66.0 (CH2 α-O), 50.9 (CH α-NH), 46.4 47.0 (CH2 α-N), 39.4 (CH2 Phe), 35.8 33.6 (CH3 NMe), 27.7 (3 CH3 Boc).

2) Cyclization to Id-p1 p-Nitrophenyl carbonate Id-p2 is treated with trifluoroacetic acid for 30'. Addition of ether gave the corresponding TFA salt which precipitated as a white solide. It was filtered and used in the next step without further purification. The TFA salt (220 mg, 0.44 mmol, 1 eq) dissolved in MeCN (10 mL) was added slowly to a solution of Diisopropylethylamine (194 μL, 1.14 mmol, 2.6 eq) and hydroxybenzotriazole (HOBt) (60 mg, 0.44 mmol, 1 eq) in 25 mL MeCN. The reaction mixture was stirred for 3 days and concentrated in vacuo. CH$_2$Cl$_2$ is then added and the organic phase was washed with 1N NaHCO3, brine, dried over Na2SO4 and concentrated in vacuo. The residue (110 mg) was then purified by silica gel chromatography.

[CHCl$_3$/MeOH/AcOH (20:0.5:0.1) then puis CHCl$_3$/MeOH [20:1]) to afford 42 mg of Id-1.

HPLC t$_R$ (Id-1) 5.88 (gradient 30-100% B, 20 min)

HRMS (ESI) calculated for C$_{13}$H$_{16}$N$_2$O$_3$ 249.1234, found 249.1230.

$^1$H NMR Id-1 (300 MHz, CDCl$_3$) δ 7.25 (m, 5H, arom-H), 6.10 (d, H$^4$), 4.75 (dd, J=8.9, 7.4 Hz, H$^5$), 4.20 (m, 2H$^3$), 4.15 (m, H$^2$), 3.28 (dd, J=14.0, 7.6 Hz, 1H$^6$), 3.17 (m, H$^{2'}$), 3.02 (dd, 1H$^6$), 3.0 (s, 3H$^1$).

$^{13}$C NMR Id-1 (100 MHz, CDCl$_3$) δ 172.3 (CO amide), 157.7 (CO carbonate), 136.9 (C-arom), 129.3 (2CH arom), 128.6 (2CH arom), 126.8 (CH arom), 69.6 (CH$_2$ α-O), 54.0 (CH α-N), 52.9 (CH$_2$ α-N), 36.6 (CH$_3$ Me), 35.7 (CH$_2$ Phe).

Example 7

Synthesis of 1,1-Dioxo-1 λ$^6$-[1,2,5,8]thiatriazocan-4-ones (Formula If)

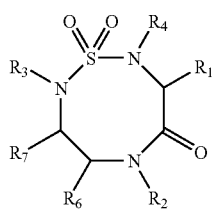

(If)

General Synthetic Scheme for If.

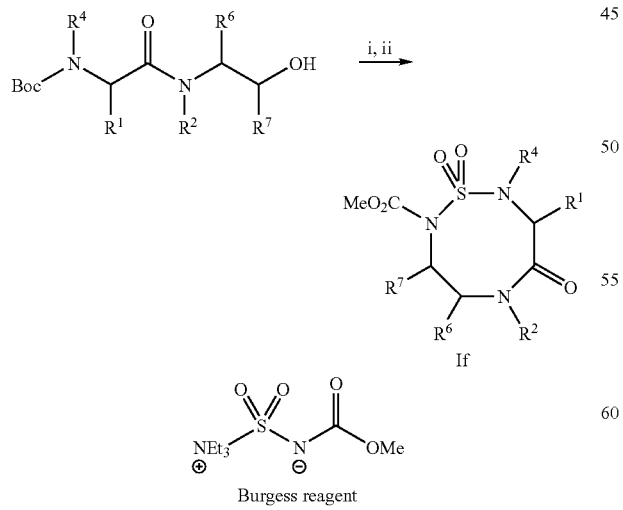

i) (a) TFA; (b) NaHCO$_3$ satured, DCM; ii) Burgess reagent (2,5 eq), THF, 70° C. for two hours.

Example 8

Synthesis of 10-methyl-6,6,11-trioxo-8,9,10,11,11a,12-hexahydro-5H-6λ$^6$-thia-5a,7,10-triaza-cycloocta[b]naphthalene-7-carboxylic acid methyl ester (Formula If-1)

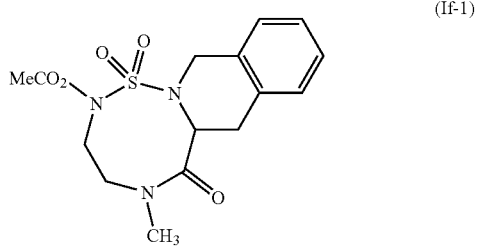

(If-1)

General Synthetic Scheme for If-1.

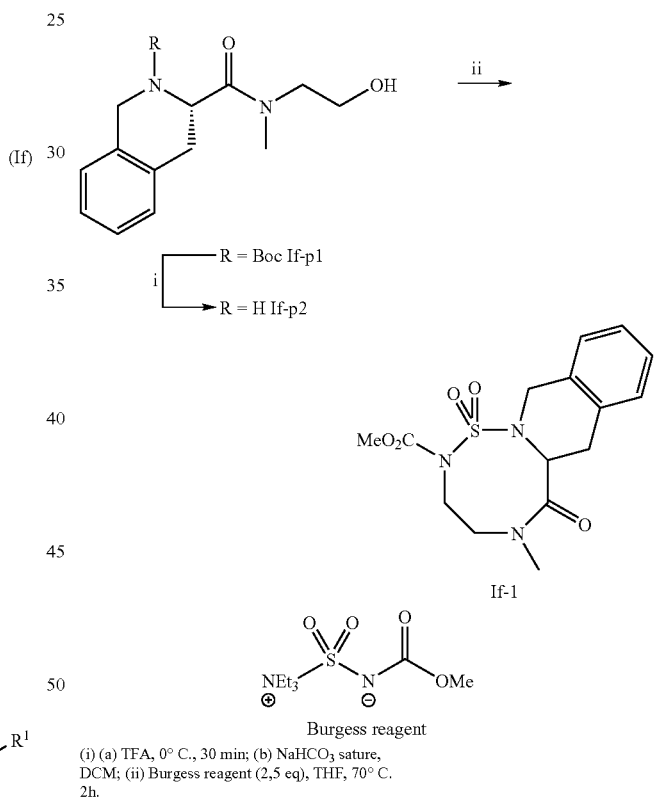

(i) (a) TFA, 0° C., 30 min; (b) NaHCO$_3$ sature, DCM; (ii) Burgess reagent (2,5 eq), THF, 70° C. 2h.

i) The N-Boc protected dipeptide alcohol was treated with TFA for 30 minutes at 0° C. The TFA was removed under vacuum and the residue was dissolved in AcOEt. Saturated NaHCO3 was added under stirring and after 10 minutes the organic phase was dried with Na2SO4 and concentrated under vacuum to give If-p1.

ii) Compound 1f-p1 (175 mg, 0.75 mmol, 1 eq), is dissolved in 10 mL anhydrous THF and Burgess reagent (534 mg, 2.24 mmol, 2.5 eq) is added. The solution is then heated under reflux at from about 70° C. to about 90° C. for 2 days. The reaction mixture is then poured into a solution of saturated NH₄Cl (40 mL). The mixture is extracted with CH2Cl2 and the organic phase is washed with H$_2$O, dried over Na$_2$SO$_4$ and concentrated under vacuum. The crude mixture is then purified by silica gel chromatography (CHCl$_3$/MeOH/AcOH (18:1:0.2) to yield If-1.

The detailed examples are given by way of example of the embodiments, and are in no way considered to be limiting to the invention. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. A method for the treatment of malaria comprising:
administering to an individual in need thereof, a therapeutic composition comprising an effective amount of a compound of the formula B:

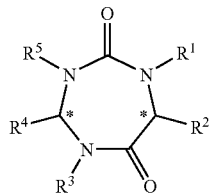

(B)

wherein R$^1$, R$^2$, R$^3$, R$^4$, and R$^5$ represent, each independent from the other, a member selected from the group consisting of: a hydrogen atom; an amino acid side chain; a (C1-C10) alkyl; (C1-C10) alkenyl; (C1-C10) alkynyl; (C5-C12) monocyclic or bicyclic aryl; (C5-C14) monocyclic or bicyclic aralkyl; monocyclic or bicyclic (C5-C14) heteroaralkyl; and (C1-C10) monocyclic or bicyclic heteroaryl group having up to 5 heteroatoms selected from N, O, S, and P said groups being able to be non-substituted or substituted by 1 to 6 substituents further selected from the group consisting of: a halogen atom, an NO$_2$, OH, amidine, benzamidine, imidazole, 1,2,3-triazole, alkoxy, (C1-C4), amino, piperazine, piperidine, dialkylamino, guanidine group, bis alkylated or bis acylated guanido group, carboxylic acid, carboxamide, ester, hydroxamic acid, phosphinic acid, phosphonate, phosphonamidate, sulfhydryl and any combination thereof; or a pharmaceutically acceptable salt thereof, together with a pharmaceutically acceptable carrier or excipient.

2. The method of claim 1, wherein the therapeutic composition further comprises an additional biologically active agent.

3. The method of claim 2, wherein the biologically active agent comprises chloroqine, a chloroquine derivative, an HIV protease inhibitor, an antiviral or a combination thereof.

4. The method of claim 1, wherein the pharmaceutically acceptable form comprises a controlled release tablet.

5. The method of claim 4, wherein the controlled release tablet further comprises an enteric coating.

6. The method of claim 1, wherein the compound of formula B is:

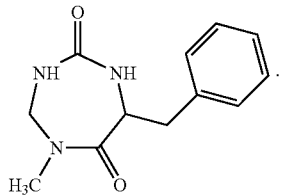

(4b)

7. The method of claim 1, wherein the compound of formula B is:

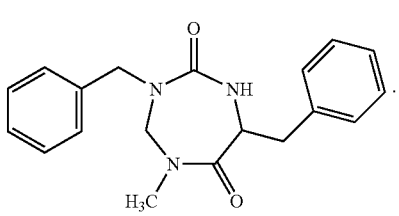

(8a)

* * * * *